(12) United States Patent
Yapici (10) Patent No.: US 11,160,884 B2
(45) Date of Patent: Nov. 2, 2021

(54) ALTERNATING CURRENT MAGNET SYSTEM FOR MAGNET-ASSISTED TRANSFECTION

(71) Applicant: Sabanci Universitesi, Istanbul (TR)

(72) Inventor: Murat Kaya Yapici, Istanbul (TR)

(73) Assignee: SABANCI UNIVERSITESI, Istanbul (TR)

( * ) Notice: Subject to any disclaimer, the term of this patent is extended or adjusted under 35 U.S.C. 154(b) by 113 days.

(21) Appl. No.: 16/412,387

(22) Filed: May 14, 2019

(65) Prior Publication Data

US 2020/0360539 A1    Nov. 19, 2020

(51) Int. Cl.
   *C12N 15/87*     (2006.01)
   *A61K 41/00*     (2020.01)
   (Continued)

(52) U.S. Cl.
   CPC .......... *A61K 49/1866* (2013.01); *A61K 33/26* (2013.01); *A61K 41/0052* (2013.01); *A61K 49/186* (2013.01); *C12N 15/87* (2013.01)

(58) Field of Classification Search
   CPC ........ A61K 9/16; A61K 33/26; A61K 39/235; A61K 41/0052; A61K 47/48; A61K 48/00;
   (Continued)

(56) References Cited

U.S. PATENT DOCUMENTS 3,648,117 A * 3/1972 Yamamoto ............. H03K 17/97
                                                   361/206
8,657,731 B2 * 2/2014 Riehl ..................... A61N 2/006
                                                   600/11
(Continued)

FOREIGN PATENT DOCUMENTS

CN       102911865 A       2/2013
KR    10-2013-0046078 A    5/2013

OTHER PUBLICATIONS

Yapici, et al., Alternating magnetic field plate for enhanced magnetofection of iron oxide nanoparticle conjugated nucleic acids, Journal of Magnetism and Magnetic Materials, vol. 469, pp. 598-605 (Year: 2019).*

(Continued)

*Primary Examiner* — Donald R Spamer
*Assistant Examiner* — Lauren A. Ryan
(74) *Attorney, Agent, or Firm* — Crowell & Moring LLP (57) ABSTRACT

The present system relates to a mains-powerable, compact and customizable alternating current magnetic field plate for magnet-assisted transfection of genes to target cells. Magnet plate is based on at least one alternating current electromagnet comprising a laminated steel stack core and a multi-layer, multi-turn coil wound longitudinally therearound. The system includes a voltage rating adjustment controller, as well as a current adjuster for selective control of magnetic force applied to genetic material for delivery. Rapid magnetic field polarity switching exacts lateral motion efficiently and uniformly, thus improving the distribution of means, (Continued)

such as SPIONS, used to transfect cells with genes of interest, and in turn enhancing gene delivery and tissue localization, especially for hard-to-transfect genes, compared to DC magnet plates.

14 Claims, 3 Drawing Sheets

(51) Int. Cl.
  *A61K 49/18* (2006.01)
  *A61K 33/26* (2006.01)
(58) Field of Classification Search
  CPC .............. A61K 48/0075; A61K 49/186; A61K 49/1866; C12M 1/42; C12N 15/87; C12N 15/861
  See application file for complete search history.

(56) References Cited

U.S. PATENT DOCUMENTS

| | | | |
|---|---|---|---|
| 9,782,494 B2 | 10/2017 | Mohapatra et al. | |
| 2007/0095499 A1* | 5/2007 | Tomes, Jr. | B22D 11/0605 164/428 |
| 2007/0106271 A1* | 5/2007 | Hood | A61K 9/0009 604/890.1 |
| 2014/0093946 A1* | 4/2014 | Mathieu | C12N 15/87 435/285.1 |

OTHER PUBLICATIONS

Hai Peng Song et al., "Gene transfer using self-assembled ternary complexes of cationic magnetic nanoparticles, plasmid DNA and cell-penetrating Tat peptide," Biomaterials, dated Feb. 2010, pp. 769-778, vol. 31, Issue 4, published online by Elsevier at URL https://doi.org/10.1016/j.biomaterials.2009.09.085.

Sarah W. Kamau Chapman et al., "Application of pulsed-magnetic field enhances non-viral gene delivery in primary cells from different origins," Journal of Magnetism and Magnetic Materials, dated Apr. 2008, pp. 1517-1527, vol. 320, Issue 8, published online by Elsevier at URL https://doi.org/10.1016/j.jmmm.2008.01.002.

Stefano Castellani et al., "Magnetofection Enhances Lentiviral-Mediated Transduction of Airway Epithelial Cells through Extracellular and Cellular Barriers," Genes, dated Nov. 23, 2016, pp. 1-13, vol. 7, Issue 11, published online by MDPI at URL https://doi.org/10.3390/genes7110103.

Christian Plank et al., "The Magnetofection Method: Using Magnetic Force to Enhance Gene Delivery," Biological Chemistry, dated Jun. 1, 2005, pp. 737-747, vol. 384, Issue 5, published online by De Gruyter at URL https://doi.org/10.1515/BC.2003.082.

* cited by examiner

ALTERNATING CURRENT MAGNET SYSTEM FOR MAGNET-ASSISTED TRANSFECTION

BACKGROUND

Technical Field

The disclosed system relates to methods and devices for delivering external gene delivery such as in the form of nucleic acids to target cells. The disclosed system more specifically concerns enhancement and facilitation of transfection via magnet-assisted methods i.e. magnetofection with the help of material such as conjugated superparamagnetic iron oxide nanoparticles (SPIONs).

Background Information

In the past one and a half decades, magnet-assisted transfection or magnetofection, referring to the delivery of nucleic acids to target cells with the help of conjugated superparamagnetic iron oxide nanoparticles (SPIONs) and external magnetic fields generated by permanent magnet plates has emerged as a viable method of transfection.

BRIEF SUMMARY

The external magnetic field, among other parameters directly affects the transfection efficiency. However, standard permanent magnet plates generate static magnetic fields which are not as effective compared to time varying dynamic fields. Unlike conventional magnet plates that provide static (DC) magnetic fields, AC magnet-based magnetofection systems and methods carry the potential to provide alternating magnetic fields which improve magnet-assisted transfection by inducing lateral motion to superparamagnetic iron oxide nanoparticles and effectively provide higher probability of cellular uptake by way of endocytosis.

In standard magnet-assisted transfection, magnet plates are used to provide "static" (DC) magnetic fields and superparamagnetic iron oxide nanoparticles (SPIONs) are attached to the gene to be delivered. The magnetic field provided by the DC magnet plate pulls the SPION-gene complexes and concentrates them around the vicinity of the target cells after which the particle-gene complexes are taken inside target cells by endocytosis. However, magnetofection defines certain issues to be tackled. Firstly, some cells such as the primary cells are especially difficult to transfect, which call for robust transfection methods with high rates of gene delivery success. In an effort to further improve the efficiency of magnet-assisted transfection, recent studies have suggested the use of time-varying and/or spatially varying dynamic fields. For this purpose, different designs have been developed which could provide pulsed magnetic fields from electromagnet structures or oscillating and rotational fields from rare-earth permanent magnets. To achieve dynamic fields, current designs are either mechanically oscillating the magnet plate with respect to the cell culture plate and thereby change the field gradient with time or use electromagnetic devices to pulsate the magnetic field with respect to time. However, existing designs are hampered with bulkiness, lack of comprehensive coverage of the entire device design and/or characterization.

One study titled "The Magnetofection Method: Using Magnetic Force to Enhance Gene Delivery" by C. Plank et al. published in Biological Chemistry (June 2003) establishes as well as underlines a rapid and efficient way of transfection (specifically in vivo) employing magnetic fields. In a study titled "Application of pulsed-magnetic field enhances non-viral gene delivery in primary cells from different origins" by S. W. Kamau et al. published in Journal of Magnetism and Magnetic Materials (320. 1517-1527), a time and space-wise varying dynamic fields are proposed, pulsed field providing designs are offered as a part thereof. A ternary magnetofection complex scheme is used in the study "Gene transfer using self-assembled ternary complexes of cationic magnetic nanoparticles, plasmid DNA and cell-penetrating Tat peptide" published in Biomaterials (2010 February; 31(4):769-78) by Song et al. to display four-fold transgene expression as well as a 60% improvement in transfection on rat spinal cord in vivo. Study titled "Magnetofection Enhances Lentiviral-Mediated Transduction of Airway Epithelial Cells through Extracellular and Cellular Barriers" by Castellani et al. in Genes/Basel (2016 November; 7(11): 103) reported as a conclusion, that magnetofection can enhance lentiviral-mediated gene transfer into airway epithelial cells in the presence of extracellular and cellular barriers.

A document known in the prior art, CN 102911865, teaches a novel cell magnetic scale instrument, which is a symmetric rotating magnetic field system in a two-layer structure, the magnetic field produced thereby becoming rotatable to strengthen and even out the magnetic field. The rotating magnetic field is purported to have an enhancing effect on magnetic nanoparticle delivery on cells in varying spatial and temporal time, addressing problem of low efficiency of current magnetic labeling and magnetic transfection equipment. U.S. Pat. No. 9,782,494 B2 discloses a method of transfecting a brain cell of a subject with a polynucleotide comprising systemically administering to the subject a composition comprising a micelle having a hydrophobic superparamagnetic iron oxide nanoparticle (SPION) core, while it averts specification of magnet-aided transfection directly as a central aspect, theorizes condensability under magnetic field and thereby make the delivery of a larger payload of DNA to the tissue possible. KR 20130045078 A discloses a method for producing superparamagnetic nanoparticles and adeno-associated viruses bound via a nitrilotriacetic acid-nickel-hexa-histidine vector, also providing a method for intracellular gene delivery using a magnet to transfer the gene transporter to a non-invasive cell type wherein the rate of gene delivery to a non-invasive cell type of the gene transporter is controlled by controlling the rate of movement of the magnet.

According to the alternating current (AC) magnet system, an AC magnet plate with adaptability to different benchtop settings such as standard 96-well culture plates, empirically displays far greater (six-fold) transfection effectiveness, which poses a great advantage for specifically hard-to-transfect genes. Furthermore, the disclosed magnet plate design employs controllable intensity and controllable field profile, a significant advantage next to the static field and rare-earth magnet plates and systems using thereof.

An interesting aspect of the disclosed system relates to providing an AC magnet plate for gene delivery to cells via magnetofection.

Another interesting aspect of the disclosed system relates to the provision of a low-cost AC magnet plate for gene delivery to cells via magnetofection.

Yet another interesting aspect of the disclosed system is to provide a portable, benchtop AC magnet plate for gene delivery to cells via magnetofection with no moving parts.

A further interesting aspect of the disclosed system relates to an AC magnet plate for gene delivery to cells via magnetofection marked with an increase in transfection efficiency.

A still further interesting aspect of the disclosed system relates to an AC magnet plate for gene delivery to cells via magnetofection marked with a superior tissue localization.

The disclosed AC magnet system includes a dynamic i.e. alternating current-running magnet plate for formation of magnetic fields for benchtop cell transfection applications. Amongst the main strengths of the AC magnet plate disclosed herein lies in its configurability, adjustability and adaptability with respect to different settings, as well as compactness regarding its straightforward design and mains-powerable supply characteristics.

The alternating current magnet plate for magnet-assisted transfection i.e. magnetofection of the AC magnet system provides an improved grade in gene transfection to target cells, with the novel effect of lateral motion induction to paramagnetic material complex holding the gene to be transfected into said target cells.

The disclosed AC magnet system therefore broadly relates to a system devised to attain targeted transfection performance in a robust manner that is compatible with standard protocols in bio lab settings such as 96-well cell culture plates, yet still adaptable and flexible to different settings; marked with an increase in overall gene delivery yield empirically measurable by way of fluorescence.

The system may include an alternating magnetic field plate with adjustable magnetic field application for usage in a bio lab setting. In an example, the system may be benchtop-compact, portable, mains-powered and suitable for use in gene delivery studies as well as therapeutic nucleic acid transfection applications.

BRIEF DESCRIPTION OF THE DRAWINGS

Accompanying drawings are given solely for the purpose of exemplifying a system having an alternating current magnet plate for targeted gene delivery applications such as transfection, whose advantages over prior art were outlined above and will be explained in brief hereinafter.

The drawings are not meant to delimit the scope of protection as identified in the claims nor should they be referred to alone in an effort to interpret the scope identified in said claims without recourse to the technical disclosure.

DETAILED DESCRIPTION

With reference to FIGS. 1-4, the system 100 may include an alternating current electromagnet-based magnet plate 102 comprising at least one electromagnet 104, and voltage rating controller 106, which may include a custom transformer. The voltage rating controller 106 designated for controlling reduction to 12V/60 Hz voltage rating from an AC source 107 supplying mains power element 108 according to one embodiment for mitigating the detrimental effects of self-interference on the receiving end of transceiver communication in full-duplex communication.

Figure 4:
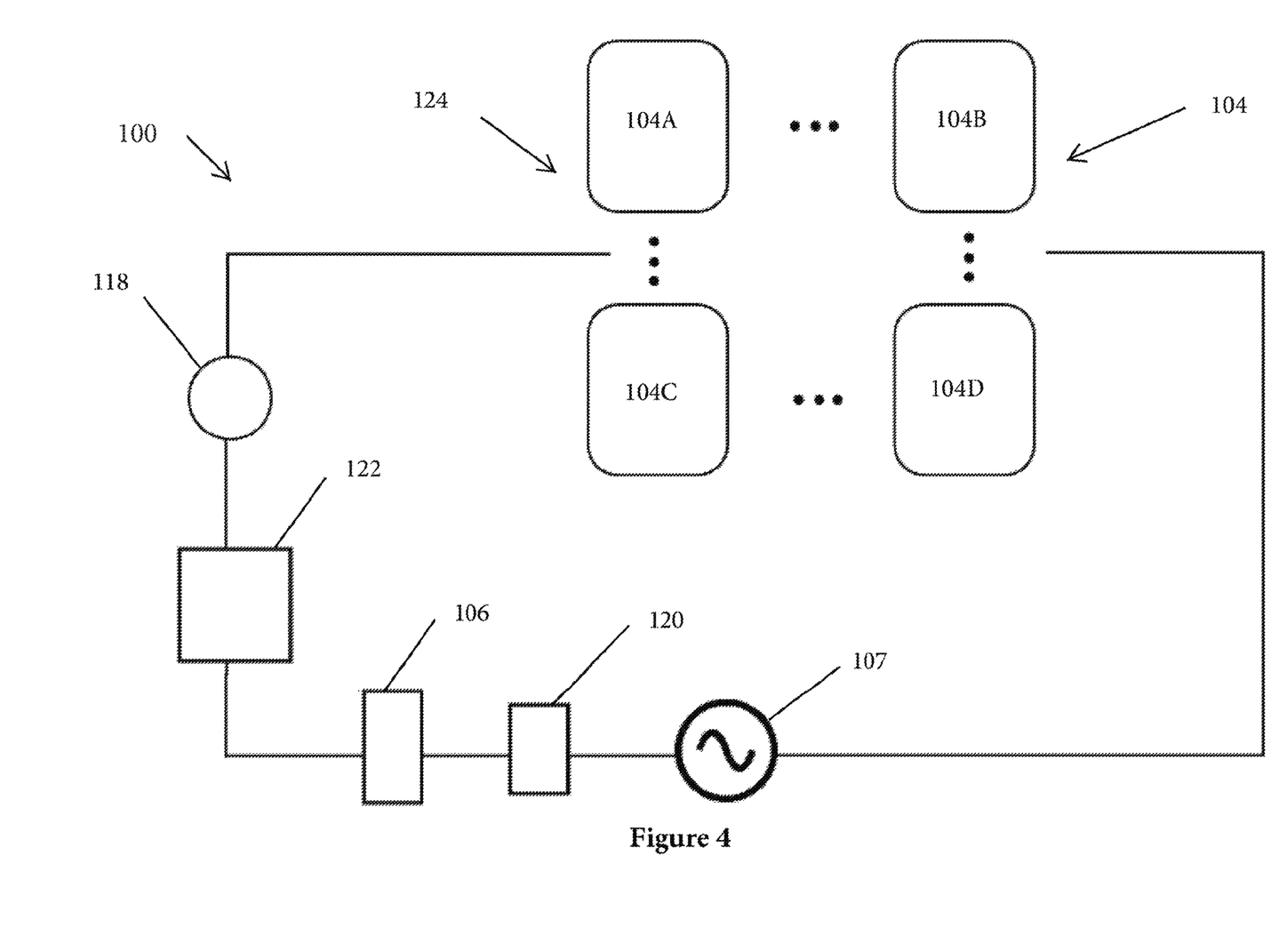
FIG. 4 is a block diagram of an example of an AC magnet system.

The disclosed AC magnet plate 102 for magnetofection is utilizable in various gene therapy applications as well as experimental setups for nucleotide material delivery in bio lab conditions.

The disclosed AC magnet plate 102 for magnetofection is based on at least one electromagnet 104, and according to one embodiment four electromagnets (104A, 104B, 104C, 104D) in series connection, each comprising a turns density of a coil 110 based on various considerations such as sufficiency of magnetic field for paramagnetic material used for transfection.

The disclosed AC magnet plate 102 can be set up in a typical bio lab environment and can be interfaced with a standard 96-well plate configuration to controllably deliver "dynamic" magnetic fields, using, for example, a controller and memory. The design does not involve any moving parts, it is directly powered from a wall outlet and can be operated in a simple plug and play fashion with immediate adaptation to standard magnetofection protocols. The unique functionality of the AC magnet plate 102 is compatible with a wide array of transfection paradigms, including but not limited to human embryonic kidney cells (HEK293) and different magnetic field and incubation conditions, wherein the improvement in transfection efficiency is well documented.

According to the disclosed system 100, development of a portable magnet plate which can provide "dynamic" alternating magnetic fields for benchtop cell transfection applications requires complicity with certain constraints regarding design and optimization. The three major design criteria are: powering from the mains supply (230/110V, 50/60 Hz) such as the AC source 107 to simplify device operation and system complexity; minimizing heat generation in the AC magnet plate 102 and maintaining the temperature at the magnet surface below the permissible range for cells and biological materials; and matching the geometry of the magnet plate with those of standard 96-well cell culture plates. To address these constraints, electromagnets with properly sized ferromagnetic core 112 and coil topology 114 were designed and arranged in series configuration to realize a magnet plate capable of delivering alternating magnetic fields at the required strength.

According to one embodiment, for powering the AC magnet plate, a transformer 106 is present to step down the large voltage at the mains supply. The voltage transformation ratio (a), which also defines the turns ratio (N1/N2) and secondary voltage of the transformer 106, is based on the current needed for the electromagnet to generate the maximum magnetic field (magnetic flux density, B-field). The magnetic field B generated by a solenoid wound around a magnetic core, is related to the magnetizing field (H-field) by the relation:

$$B = \mu_0 \mu_r H$$

Where $\mu_0$ is the magnetic permeability of free space and $\mu_r$ is the relative permeability of the core. Similarly, by applying the Ampère's Law, the magnetizing field for an ideal solenoid can be expressed as below:

$$H = \mu_0 \frac{n}{L} I$$

where (n/L) is the turn density, and (I) is the applied current. By adjusting the turn density and input current, a sufficiently large H-field is developed to drive the ferromagnetic core into saturation and maximize the B-field output.

According to one embodiment, while maximizing the B-field, heating of the magnet is kept at minimum. To achieve this, the turn density, input current, and secondary voltage of the transformer are carefully designed considering the interplay between heating effects, size limitations imposed by the dimensions of possible cell culture plates in various applications, cross sectional area of the conducting wires in the solenoid, and geometry of the core.

Figure 1:
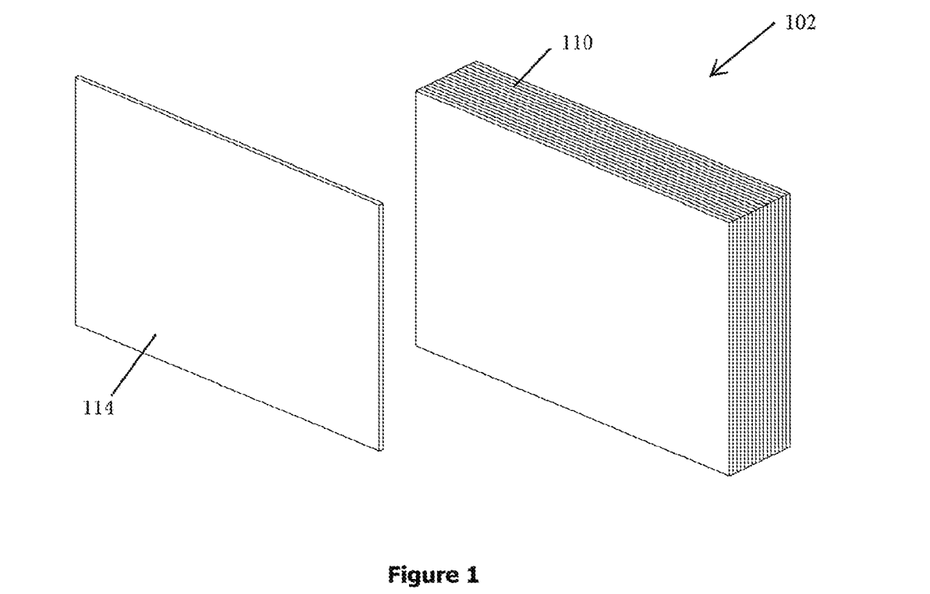
FIG. 1 demonstrates the isometric view of the laminated stack of the ferromagnetic core.

In cell culturing, rectangular 96-well plates are frequently used, and they have dimensions of approximately 127 mm×85 mm with 9 mm center-to-center spacing between wells. In an embodiment, the magnetic and geometrical constraints of a specific case are considered, 15 rectangular-cut laminations 114 which are ~2.6 cm-wide, 5 cm-long, and 0.5 mm-thick, are stacked to form the ferromagnetic core 110 (FIG. 1). Geometry of this embodiment results in the magnetic flux emanating from one electromagnet acting incident on four wells. By having multiple electromagnets, the effective coverage area is therefore increased. According to an embodiment, conducting coil is constructed with gauge-16 insulated copper magnet wires of ~1.3 millimeter-squared cross sectional area. According to an embodiment, the system comprises a coil tightly wound along the length of the core in multiple layers which were positioned on top of each other and held intact by insulating attachment means. By winding in multiple layers, larger number of turns could be allocated in a fixed length to maximize the turn density (n/L) and generate larger magnetizing field for the same applied current (I). In an embodiment, a total of 162 turns are wound in 9 layers which approximately correspond to 18 turns per layer, and the resistance of the coil is thus measurable at ~0.6Ω. In different embodiments, coils may be hand-wound or automated winding machines may be utilized to wrap the coil and precise sizing of cores with laser machining techniques, electromagnets matching the size of individual wells may be constructed and duplicated to cover the entirety of wells in a well plate, irrespective of the plate size.

Figure 2:
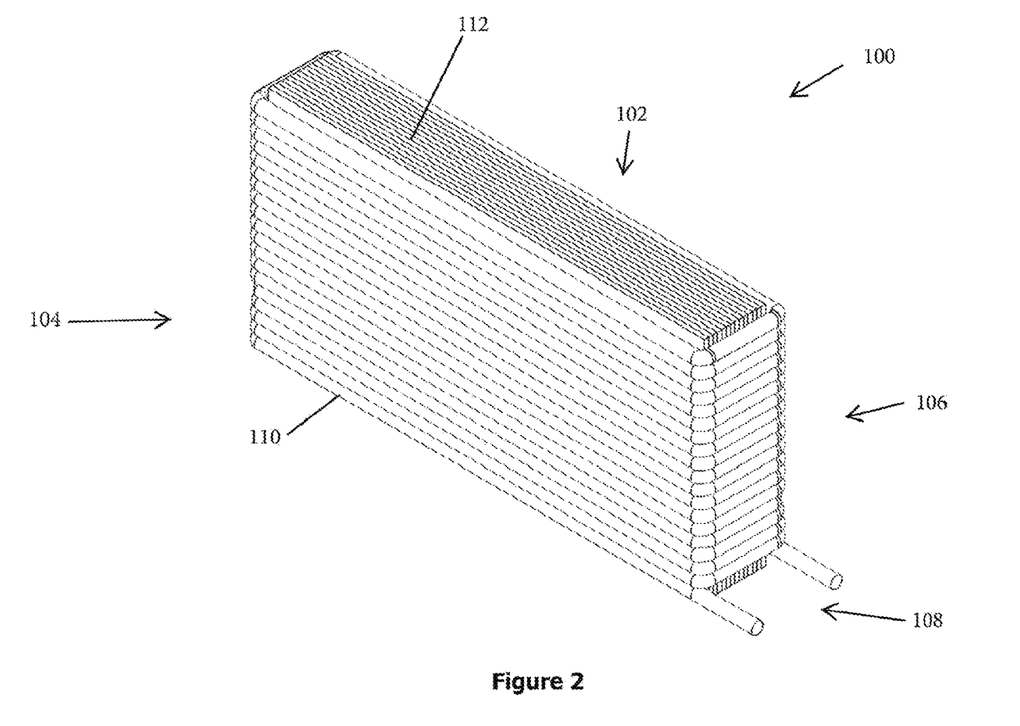
FIG. 2 demonstrates the isometric view of the final electromagnet core-coil geometry.
Figure 3:
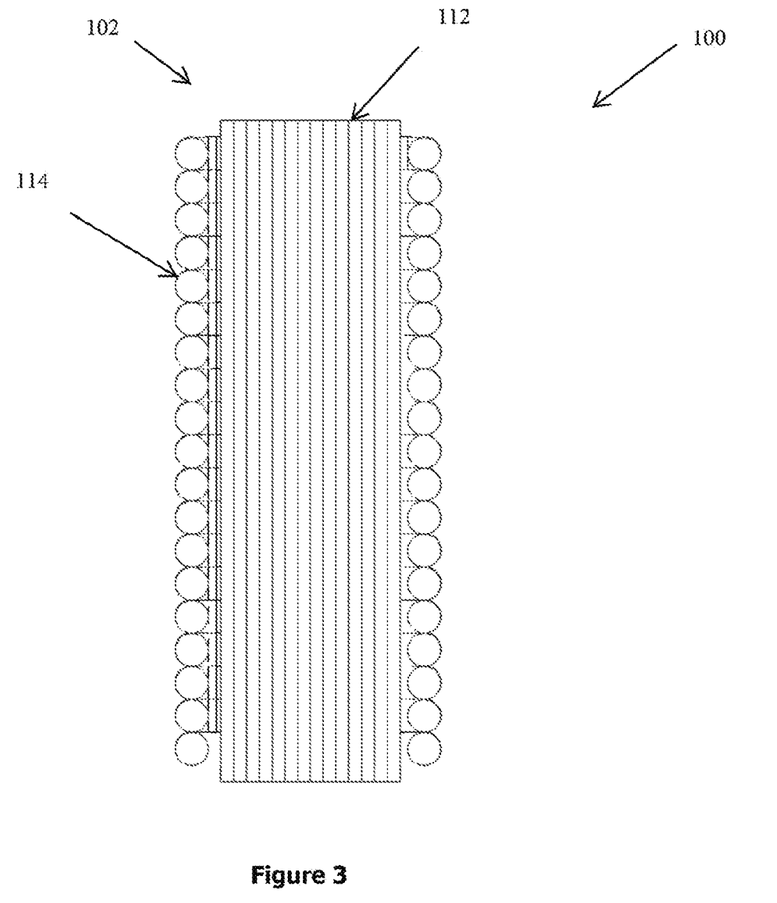
FIG. 3 demonstrates the cross-sectional view of the final electromagnet core-coil geometry.

According to an embodiment, the multi-layer, multi-turn coil is modeled as an array of circular copper conductors, while the magnetic core is modeled as an integral element made of silicon steel. Thus, the magnetic field generated by the electromagnet under a DC current of 4 A applied to the conductors as a boundary condition is resulted in average magnetic flux density in the range of ~20-30 milli Teslas (mT) at the magnet surface. In one embodiment, magnetic flux density of the electromagnet is relatively uniform over the surface of the electromagnet. Larger values in the vicinity of ~110 mT are to be expected at sharp corners of the electromagnet due to edge effects; with the relationship between magnetic flux density and the distance above the magnet surface emerging as follows: The field drops from 21.57 mT to 0.81 mT within a distance of 2 centimeters. Thus, considering the thickness margin of ~1-2 mm for the bottom of a typical well plate, the effective magnetic field exposure on the bottom of a well is configured to be in the range of 20.5 mT-18.9 mT.

In one embodiment, the magnetic force (Fm) acting on a superparamagnetic particle subject to magnetic flux density (B) can be expressed as below:

$$\vec{F}_m = (\vec{m} \cdot \nabla)\vec{B}$$

This equation is further reducible if the total magnetic moment of the particle (m) is assumed to be constant, and the flux density (B) is acting primarily in the z-direction. Then, magnetic force can be approximated as follows:

$$F_m = m\frac{\partial B_z}{\partial z} = \frac{V\Delta\chi B_z}{\mu_0}\left(\frac{\partial B_z}{\partial z}\right)$$

where V is the volume of the particle and $\Delta_\chi$ is the effective volumetric magnetic susceptibility of the particle with respect to the medium. In magnetofection applications based on standard 96-well cell culturing plates, wells have a typical depth of ~15 mm and usually some volume remains unfilled. Therefore, in the system it is ensured that, even particles that are suspended as high as 10 mm above the magnet surface still get exposed to magnetic flux densities of ~6-7 mT and field gradients of approximately 1.5 T/m, which result in magnetic forces on the order of pN-fN on superparamagnetic iron oxide nanoparticles according to one embodiment.

In an embodiment, the electromagnet is connected to a transformer with a turns ratio of 20 in order to step-down a mains supply of 240V/60 Hz to 12V/60 Hz. Due to the small coil resistance, very large currents could flow in the electromagnet which would cause excessive heating. To minimize heating, the current was limited using a series-connected rheostat with a relatively low resistance ~22Ω and a high power rating of 50 W which still allowed tuning of the current up to several amperes for developing sufficient magnetizing field.

In an embodiment, all the components of the AC magnet plate are housed in an enclosure compatible with standard 96-well plate in concordance with a specific bio lab application setting. In an embodiment, said enclosure may be manufactured using 3D printing technology. In an embodiment, AC magnet plate comprises four electromagnets, manually-wound with approximately the same number of turns and connected in series configuration. In a specific case, positioning the 96-well plate on top of the electromagnet array, 16 wells could be exposed to magnetic field in a simultaneous fashion. Application of a driving current of approximately 3.9 A rms to the coils results in a peak magnetic field of ~237 gauss (G). The relationship between the magnetic field and applied driving current is linearly increasing, as well as the spatial distribution of the magnetic field over the electromagnet surface being substantially uniform, with higher values occurring at the corners of the electromagnet due to the tighter winding and narrower spacing of the conducting coil at the edges. In an embodiment, over a duration of 20 minutes, while the coil was driven at a current of 3.9 A, the media temperature increases from room conditions (~20° C.) to a maximum of 28.1° C. which is suitable for survival of most cells and biological materials.

AC magnet plate of the system is distinctively superior when compared against conventional neodymium-iron-boron (NdFeB) DC magnet plates in transfection applications. In a setting where a transfection cycle involves four days, multi-well plates host incubation for an initial 24 hour duration, following which the second day, the magnetic nanoparticles and plasmids are added, and transfection is performed using the alternating current magnetic fields generated by the magnet plate. In the remaining two days, the plates are kept in the incubator, and after 24-hour and 48-hour incubation periods, fluorescence levels are measured using a microplate reader and cell imaging is conducted with a fluorescence microscope.

During the experiments, we have employed two different magnetic plates including a commercial DC magnet plate and the AC magnet plate developed according to the teaching of this disclosure. The DC magnet plate is comprised of an array of neodymium-iron-boron (NdFeB) magnets arranged in 96-well plate configuration and provides unidirectional static magnetic fields up to 250 mT which is useful to attract the magnetic nanoparticle conjugated genes towards the cultured cells. On the other hand, the AC magnet plate houses electromagnets to create alternating magnetic fields (~25 mT, 60 Hz) which are expected to enhance the transfection efficiency.

The system is based on the premise of 60 Hz alternating magnetic field having effect towards improving cell transfection. Cells selected for gene transfection, when exposed to AC magnetic fields as opposed to pure DC fields, and cell populations that are exposed to the AC magnetic field conditions display enhanced levels of fluorescence indicating efficiency increase. This technical effect is achieved by the AC magnetic field allowing rapid switching of the magnetic field polarity via a switch 120, imparting critical lateral motion on the particles and allowing a more uniform distribution of the SPIONs on the cell membrane, effectively increasing the probability of cellular uptake by endocytosis.

In a nutshell, what is disclosed is a low-cost, benchtop, portable, reconfigurable alternating current magnet plate with properties to enhance transfection efficiency in magnetofection applications which are conventionally based on direct current, rare-earth based magnet plates. The alternating current magnet plate in the system may be readily and directly applied to 96-well cell culturing plates in standard applications, requiring no additions or modifications to standard transfection protocols. The effect of the alternating (AC) magnetic fields that are applied as opposed to purely static (DC) fields as done in conventional magnetofection are enabled by the rapid magnetic field polarity switching that exacts lateral motion efficiently and uniformly, thus improving the distribution of means, such as SPIONs, used to transfect cells with genes of interest.

According to an embodiment, the number of wells can range from a single well to all wells existing in the cell culture plate.

According to an embodiment, the intensity of magnetic field can be controlled using, for example, a processor and memory.

According to an embodiment, the duration of magnetic field exposure can be controlled using, for example, the processor and memory.

According to an embodiment, the ON time to OFF time of AC field can be controlled using, for example, the processor and memory.

According to an embodiment, it is possible to deliver AC field for X minutes, followed by DC field for Y minutes; using the same magnet plate described in this disclosure.

According to an embodiment, the disclosed magnet plate can achieve complex field beyond what is available with standard DC magnet plates, or those that utilize alternative methods of mechanically generating a changing magnetic field profile.

According to an embodiment, the magnetic field exposure can be electrically turned on/off, without separating the cell culture plate from the magnet plate, opposite to what is achieved by standard DC plates which requires physical separation between the cell culture plate and the magnet to stop/reduce magnetofection. This is potentially useful if/when wells need to be exposed to multiple (subsequent) transfection steps or various chemicals, without causing any physical disturbance to the cell culture plate.

According to an embodiment, the electromagnets can be selected by way of row/column address mechanism 124 in a variety of configurations to select specific wells in which the transfection event is activated/effectuated. In an example, the electromagnet selection using row/column addressing may be performed with a microprocessor executing instructions stored in memory.

In an embodiment, culture plates on which transfection will be effectuated are subjected to AC field for a given amount of time, subsequent to which DC field may be applied for another amount of time. Between these two periods, a period may be allotted for purposes such as incubation or standby. These three periods may be arranged in different orders in accordance with the needs or goals of the transfection application.

In an embodiment, an AC-powered magnetic field plate for controllable magnetic field-driven genetic material delivery and transfection to cells is disclosed.

According to an aspect, said magnetic field plate comprises at least one alternating current electromagnet further comprising a ferromagnetic core of laminated steel stack and a multi-layer, multi-turn coil wound longitudinally therearound.

According to an aspect, said magnetic field plate further comprises at least one voltage rating controller 106.

According to an aspect, said magnetic field plate further comprises a current adjuster 118 such that a current signal at least as much as a predetermined threshold value required for effectuating transfection to cells is adjustably generated.

According to another aspect, said at least one voltage rating controller 106 is or comprises a transformer.

According to another aspect, said magnet plate comprises multiple alternating current electromagnets spatially arranged to deliver alternating magnetic fields to multiple wells on-demand.

According to another aspect, said current adjuster 118 is or comprises a rheostat.

According to another aspect, laminated steel stack core comprises silicon steel laminations of dimensions based on the effective region to which magnetic flux will be delivered.

According to another aspect, said coil comprises a winding with a specific turns ratio and number of layers producing a predetermined magnetic flux density.

According to another aspect, said predetermined threshold value required for effectuating transfection to cells is periodically incremented or decremented.

According to another aspect, said magnetic field plate further comprises a power switching means for magnetic field exposure control. In example, the power switching means is a power switch. 120

According to another aspect, said magnetic field plate comprises intensity and duration control means 122.

According to another aspect, said magnetic field plate is configured to deliver AC field and/or DC field on-demand.

According to another aspect, said magnetic field plate further comprises a row-column based spatial address mechanism 124 to effectuate transfection events in specific wells.

The methods, devices, processing, circuitry, and logic described herein may be implemented in many different ways and in many different combinations of hardware and software. For example, all or parts of the implementations may be circuitry that includes an instruction processor, such as a Central Processing Unit (CPU), microcontroller, or a microprocessor; or as an Application Specific Integrated Circuit (ASIC), Programmable Logic Device (PLD), or Field Programmable Gate Array (FPGA); or as circuitry that includes discrete logic or other circuit components, including analog circuit components, digital circuit components or both; or any combination thereof. The circuitry may include discrete interconnected hardware components or may be combined on a single integrated circuit die, distributed among multiple integrated circuit dies, or implemented in a Multiple Chip Module (MCM) of multiple integrated circuit dies in a common package, as examples.

Accordingly, the circuitry may store or access instructions for execution, or may implement its functionality in hardware alone. The instructions may be stored in a tangible storage medium that is other than a transitory signal, such as a flash memory, a Random Access Memory (RAM), a Read Only Memory (ROM), an Erasable Programmable Read Only Memory (EPROM); or on a magnetic or optical disc, such as a Compact Disc Read Only Memory (CDROM), Hard Disk Drive (HDD), or other magnetic or optical disk; or in or on another machine-readable medium. A product, such as a computer program product, may include a storage medium and instructions stored in or on the medium, and the instructions when executed by the circuitry in a device may cause the device to implement any of the processing described above or illustrated in the drawings.

The implementations may be distributed. For instance, the circuitry may include multiple distinct system components, such as multiple processors and memories, and may span multiple distributed processing systems. Parameters, databases, and other data structures may be separately stored and managed, may be incorporated into a single memory or database, may be logically and physically organized in many different ways, and may be implemented in many different ways. Example implementations include linked lists, program variables, hash tables, arrays, records (e.g., database records), objects, and implicit storage mechanisms. Instructions may form parts (e.g., subroutines or other code sections) of a single program, may form multiple separate programs, may be distributed across multiple memories and processors, and may be implemented in many different ways. Example implementations include stand-alone programs, and as part of a library, such as a shared library like a Dynamic Link Library (DLL). The library, for example, may contain shared data and one or more shared programs that include instructions that perform any of the processing described above or illustrated in the drawings, when executed by the circuitry.

In some examples, each unit, subunit, and/or module of the system may include a logical component. Each logical component may be hardware or a combination of hardware and software. For example, each logical component may include an application specific integrated circuit (ASIC), a Field Programmable Gate Array (FPGA), a digital logic circuit, an analog circuit, a combination of discrete circuits, gates, or any other type of hardware or combination thereof. Alternatively or in addition, each logical component may include memory hardware, such as a portion of the memory, for example, that comprises instructions executable with the processor or other processors to implement one or more of the features of the logical components. When any one of the logical components includes the portion of the memory that comprises instructions executable with the processor, the logical component may or may not include the processor. In some examples, each logical components may just be the portion of the memory or other physical memory that comprises instructions executable with the processor or other processor to implement the features of the corresponding logical component without the logical component including any other hardware. Because each logical component includes at least some hardware even when the included hardware comprises software, each logical component may be interchangeably referred to as a hardware logical component.

Various implementations have been specifically described. However, many other implementations are also possible.

The invention claimed is:

1. A system comprising:
a magnetic field plate powered by an alternating current, a direct current, or a combination thereof, for controllable magnetic field-driven genetic material delivery and transfection to cells;
said magnetic field plate comprising at least one alternating current electromagnet, said at least one alternating current electromagnet including a ferromagnetic core of laminated steel stack and a multi-layer, multi-turn coil wound longitudinally therearound;
said magnetic field plate further comprising at least one voltage rating controller; and
said magnetic field plate further comprising a current adjuster to deliver to the magnetic field plate, for a first predetermined time, the alternating current, before, or after delivery, for a second predetermined time, of the direct current such that a current signal at least as much as a predetermined threshold value required for effectuating transfection to cells is adjustably generated during the first and second predetermined times.

2. The system of claim 1, wherein said at least one voltage rating controller is a transformer.

3. The system of claim 1, wherein said magnet plate comprises multiple alternating current electromagnets spatially arranged to deliver alternating magnetic fields to multiple wells on-demand.

4. The system of claim 1, wherein said current adjuster is a rheostat.

5. The system of claim 1, wherein said ferromagnetic core of laminated steel stack comprises silicon steel laminations of dimensions based on an effective region to which magnetic flux will be delivered.

6. The system of claim 1, wherein said coil comprises a winding with a specific turns ratio and number of layers producing a predetermined magnetic flux density.

7. The system of claim 1, wherein said predetermined threshold value required for effectuating transfection to cells is periodically incremented or decremented.

8. The system of claim 1, wherein said magnetic field plate further comprises a power switch to control magnetic field exposure.

9. The system of claim 1, wherein said magnetic field plate comprises an intensity and duration controller to control the magnetic field.

10. The system of claim 9, wherein the intensity and duration controller is a microprocessor executing instructions stored in memory.

11. The system of claim 1, wherein said magnetic field plate is configured to deliver AC field and/or DC field on-demand.

12. The system of claim 1, wherein the at least one alternating current electromagnet is a plurality of alternating current electromagnets, and said magnetic field plate is configured to perform row-column based spatial addressing of the alternating current electromagnets to effectuate transfection events in specific wells by generation of corresponding alternating magnetic fields with one of the alternating current electromagnets.

13. The system of claim 1, wherein the at least one alternating current electromagnet is a plurality of alternating current electromagnets, and the current adjuster is configured to selectively and independently energize the alternating current electromagnets to generate corresponding alternating magnetic fields.

14. The system of claim 1, wherein the current adjuster is further configured to insert for a predetermined time, between the alternating current and the direct current, an incubation period.

* * * * *